United States Patent
Hoder et al.

(10) Patent No.: US 11,511,221 B2
(45) Date of Patent: Nov. 29, 2022

(54) PARTICLE FILTER AS WELL AS METHOD FOR THE MANUFACTURE THEREOF

(71) Applicant: Dräger Safety AG & Co. KGaA, Lübeck (DE)

(72) Inventors: Matthias Hoder, Lübeck (DE); Stephan Hake, Pansdorf (DE); Mathias Ahrens, Techau (DE); Andrea Görndt, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 476 days.

(21) Appl. No.: 16/707,503

(22) Filed: Dec. 9, 2019

(65) Prior Publication Data

US 2020/0108341 A1 Apr. 9, 2020

Related U.S. Application Data

(62) Division of application No. 15/337,345, filed on Oct. 28, 2016, now Pat. No. 10,537,841.

(30) Foreign Application Priority Data

Oct. 30, 2015 (DE) .......................... 102015014017.5

(51) Int. Cl.
*B01D 46/00* (2022.01)
*A62B 18/02* (2006.01)
(Continued)

(52) U.S. Cl.
CPC .......... *B01D 46/0001* (2013.01); *A62B 18/02* (2013.01); *A62B 23/02* (2013.01);
(Continued)

(58) Field of Classification Search
CPC .... B01D 46/0005; B01D 46/10; B01D 46/28; B01D 46/121; B01D 2201/12;
(Continued)

(56) References Cited

U.S. PATENT DOCUMENTS 6,485,544 B1 11/2002 Ziske
7,077,921 B1 * 7/2006 Dimicelli ............... B01D 46/58
55/497

(Continued)

FOREIGN PATENT DOCUMENTS

CN 1679994 A 10/2005
CN 1960792 A 5/2007
(Continued)

*Primary Examiner* — Minh Cha T Pham
(74) *Attorney, Agent, or Firm* — McGlew and Tuttle, P.C.

(57) ABSTRACT

A method for manufacturing a filter (1) for gas masks includes providing a flat paper and folding the paper into a pleated preform. The filter element (2) is separated from the pleated preform (6) and is inserted into a housing (3). The inserted filter element (2) is connected to the housing (3) at least at some points. This filter elements (2) may have a polygonal outer contour, upon separating the element from the pleated filter preform (6). A foam and/or an adhesive is applied to an outer edge of the filter element (2), arranged on the circumference of the filter element, for an at least partial sealing of an edge (5). This establishes a connection to the housing (3) in at least some sections.

8 Claims, 5 Drawing Sheets

(51) Int. Cl.
    *B01D 46/10* (2006.01)
    *A62B 23/02* (2006.01)
    *B01D 46/52* (2006.01)
    *A61M 16/10* (2006.01)
    *A62B 7/10* (2006.01)

(52) U.S. Cl.
    CPC ......... *B01D 46/0005* (2013.01); *B01D 46/10* (2013.01); *B01D 46/521* (2013.01); *B01D 46/523* (2013.01); *A61M 16/105* (2013.01); *A62B 7/10* (2013.01); *B01D 2201/12* (2013.01); *B01D 2201/34* (2013.01); *B01D 2201/40* (2013.01); *B01D 2265/04* (2013.01); *B01D 2275/20* (2013.01); *B01D 2275/206* (2013.01); *B01D 2277/30* (2013.01); *B01D 2279/00* (2013.01)

(58) Field of Classification Search
    CPC  B01D 2201/34; B01D 46/521; B01D 46/523; A62B 23/02; A62B 18/02
    USPC ........................... 55/467, 482, 497, 496, 427
    See application file for complete search history.

(56) References Cited

U.S. PATENT DOCUMENTS

| | | | |
|---|---|---|---|
| 7,442,221 B2 | 10/2008 | Ruhland et al. | |
| 7,931,726 B2 * | 4/2011 | Karlsson | B01D 46/10 55/482 |
| 7,938,927 B2 * | 5/2011 | Sundvik | B01D 46/521 55/497 |
| 8,163,054 B1 | 4/2012 | McGrath et al. | |
| 8,409,312 B2 * | 4/2013 | Gorg | B01D 46/521 55/497 |
| 9,630,131 B2 * | 4/2017 | Sudermann | F02M 35/02408 |
| 2005/0150201 A1 | 7/2005 | Choi et al. | |
| 2006/0037296 A1 * | 2/2006 | Duffy | B01D 46/521 55/495 |
| 2007/0006560 A1 * | 1/2007 | Ruhland | B01D 46/10 55/497 |
| 2008/0011672 A1 * | 1/2008 | Schwartz | B01D 46/121 55/467 |
| 2008/0017570 A1 | 1/2008 | Choi et al. | |
| 2014/0318092 A1 * | 10/2014 | Rieger | B01D 46/0005 55/511 |
| 2015/0059297 A1 * | 3/2015 | Ruhland | F02M 35/09 55/427 |
| 2015/0096273 A1 * | 4/2015 | Kaiser | B01D 46/2411 55/502 |

FOREIGN PATENT DOCUMENTS

| | | |
|---|---|---|
| CN | 101703828 A | 5/2010 |
| CN | 102380272 A | 3/2012 |
| DE | 69412268 T2 | 3/1999 |
| DE | 202005009836 U1 | 10/2006 |
| GB | 527851 A | 10/1940 |
| GB | 2411367 A | 8/2005 |
| JP | 2002065880 A | 3/2002 |
| WO | 9505235 A1 | 2/1995 |
| WO | 2005102497 A1 | 11/2005 |
| WO | 2011146294 A2 | 11/2011 |

\* cited by examiner

PARTICLE FILTER AS WELL AS METHOD FOR THE MANUFACTURE THEREOF

CROSS REFERENCE TO RELATED APPLICATIONS

This application is a divisional of, and claims the benefit of priority under 35 U.S.C. § 120, of U.S. application Ser. No. 15/337,345 filed Oct. 28, 2016 now U.S. Pat. No. 10,537,841 B2, which claims the benefit of priority under 35 U.S.C. § 119 of German Application 10 2015 014 017.5 filed Oct. 30, 2015, the entire contents of which are incorporated herein by reference.

FIELD OF THE INVENTION

The present invention pertains to a method for manufacturing a filter for respirators, for medical filters and device filters, especially for manufacturing the particle-filtering element. In the method described, at first a pleated preform is manufactured from a flat filter medium, from which at least one filter element is separated, wherein a means for producing an edge seal in the area of the outer edges of the filter element is applied to the pleated preform and/or to the filter element before, during or after separating the filter element. This filter element may finally be inserted into a housing and be glued in at least some points with the housing in the area of the edge seal. In this way, a filter, especially a particle filter, is provided, which has a housing as well as a filter element made of a folded filter paper inserted into the housing and connected to the housing.

Prior-art filters are different and include gas filters, particle filters, as well as combined gas particle filters. The present invention pertains essentially to a particle filter or the particle filter part of a combination filter as well as to a method for the manufacture thereof. In this case, the configuration of the particle-filtering element as well as the sealing thereof against the housing are essential to the present invention. Such a filter may preferably be combined with a gas filter and is especially used for respirators or medical filters or as device filters.

BACKGROUND OF THE INVENTION

It is always problematic in providing filter elements that such filter elements represent a flow resistance, which must be overcome by the user during breathing. This results in a burden for the user, which occurs in addition to the actual activity.

Such a filter element with a folded filter paper part is known, for example, from DE 694 12 268 T2. The described filter element has essentially a rectangular housing, into which a folded filter paper as the filter element is inserted. The folding of the filter paper takes place in this case, above all such that an as large as possible flow cross section is achieved, so that the flow resistance of the filter element is reduced. In addition to the above-described filter elements with a rectangular housing and a folded filter element, so-called ring filters, in which the folds of the filter are arranged concentrically, are, moreover, known. Ring filters are often used as particle-filtering elements especially for round housings. These ring filters consist of filter paper parts which are produced directly during the manufacture of the filter paper in the form of ring folds. Because of their design, ring filters are easy to seal in round housings in a particle-impermeable manner, for example, by clamping. However, a drawback of such ring filters is that because of their manufacture, wide folds and large fold distances and thus only a very small filter surface can be produced, so that the flow resistances and thus the resistances during breathing are comparatively great for the user.

For this reason, particle-filtering filters are often manufactured by corresponding filter elements being produced from pleated preforms of an element consisting of flat paper. In this case, the filter paper, which is, as a result, made available as roll material, is arranged into parallel folds in a zig-zag manner. The stability of the pleated preform is ensured by so-called spacers, which are connected to the folds of the filter element and hold same in their shape. Such pleated preforms are, as known from DE 69 412 268 T2, inserted into a rectangular housing and sealed against same by a connection being established between the frame and the outer edge of the pleated preform and the edge sealing thereof by means of hot glue.

Rectangular pleated preforms offer the advantage of an edge seal which can be comparatively easily produced, but are limited in this shape, namely, the rectangular shape, since the edge seal is only created at right angles to the running direction of the paper. Furthermore, the combination of traces of glue applied hot and edge seals and hot glue for the sealing of same in the housing of the particle filter for reasons of process safety is not optimal. The greater the gap between the filter element and the housing and thus the space provided for the seal is, the smaller is the usable filter surface.

In case of the use of round housings, as they are used, for example, in filters with RD-40 connection according to EN 148-1 or ISO 17420-3, round pleated preforms are cut out of the folded paper in order to utilize the maximum possible surface of the filter housing. In this case, the gap between the pleated preform and the housing is usually filled by casting or a glue is injected into the gap for the edge seal and sealing with the housing.

It is problematic in the prior-art particle filters and especially in the method for the manufacture thereof that during the manufacture of suitable filter elements, the sealing is carried out by applying an edge seal directly during the preparation of the pleated preform and, as a result of this, a part of the available filter surface is not usable. Further, large quantities of filter paper waste are often generated, which has to be discarded as scrap. This represents a considerable cost. Furthermore, it is often comparatively complicated in terms of production technology to create a reliable seal between the pleated preforms and the filter housings receiving same.

SUMMARY OF THE INVENTION

Based on the above-described technical solutions and the problems resulting therefrom, an object of the present invention is to perfect a particle-filtering filter as well as the manufacture thereof such that a reliable seal between the filter element and the housing is achieved with comparatively simple means, on the one hand, and, on the other hand, the filter paper scrap, which is generated during the preparation of suitably shaped pleated preforms, is minimized, above all, without significantly increasing the breathing resistance of the filters. The technical solution to be provided shall be able to be integrated hereby in standard production processes in a simple manner or else shall represent a comparatively simple production process.

According to the invention, a method is provided for manufacturing a filter for gas masks. The method comprises providing a flat paper material, folding the flat paper material to form a pleated preform, separating the pleated preform into at least one filter element, providing a housing, inserting the filter element into the housing and establishing a connection between the inserted filter element and the housing at least at some points. The connection is established by applying a foam or an adhesive or both a foam and an adhesive to an outer edge of the filter element, which outer edge is arranged on a circumference of the filter element, for the at least partial sealing of the edge, which sealing establishes the connection of the filter element to the housing in at least some sections.

According to another aspect of the invention, a method is provided for the manufacture of a filter for gas masks. The method comprises providing a flat paper material, folding the flat paper material to form a pleated preform, separating the pleated preform into at least one filter element with at least three corners in a plane, which is at right angles to the principle inflow direction of the filter, providing a housing with a housing wall, which housing wall is curved in at least some sections or has at least three corners, inserting the filter element into the housing with the housing wall enclosing the filter element at outer edges of the filter element and establishing a connection between the inserted filter element and the housing at least at some points.

The present invention pertains to a method for manufacturing a filter for respirators, for medical filters and device filters, in which a flat filter medium is provided and is folded into a pleated preform and at least one filter element is separated from the pleated preform. The filter element can then be inserted into a housing and be connected to the housing in at least some points, for example, by means of a suitable clamping or by gluing or embedding.

As an alternative, the filter element may be foamed by molded foams such that a connection geometry, by means of which the particle filter can be connected in a particle-impermeable manner to a filter housing, a mask or another breathing port or to a blower filter device, preferably by means of clamping, is formed by the foam and/or inserted parts. In this case, the molded foam element connecting to the filter element preferably establishes an indirect, especially particle-impermeable, connection between the filter element and a housing element, a mask or a component, through which an air stream is guided.

The solution according to the present invention is characterized in that the filter element separated from the pleated preform is inserted into the housing or is enclosed by a mold, and especially by a molded foam element, wherein it is ensured that a foam and/or an adhesive is applied to an outer edge of the filter element arranged on the circumference for the at least partial sealing of the edge. Provided that the filter is inserted into a housing and is connected to same, a particle-impermeable connection between the filter element and the housing is established in at least some sections in this way. In case of using a mold or a molded foam element, which encloses the filter element at its outer edges, the outer contour of the foamed particle filter represents a connection geometry. Thus, the creation of an edge seal by means of a foam or adhesive is an essential technical feature of the present invention, so that an optimal use of surface of the filter medium is achieved, on the one hand, and the available installation space is better utilized than in prior-art solutions, on the other hand. It is also advantageous in this case that the circumferential sealing of the edge and connection of the filter element to the housing are carried out in one working step.

An essential feature of the present invention for manufacturing a filter is that the filter element is separated from the pleated preform in such a way that the filter element has at least three corners in a plane, which is at right angles to the principal inflow direction of the filter and thus is advantageous for filters, which are at least partly connected by rotation to a device or breathing port. These may be both round and polygonal housings. According to this embodiment, a plane, which is arranged at right angles to the principal inflow direction of the filter, is defined as a plane, in which lies a cross-sectional surface of the filter element located in its inserted position in the housing.

It is essential in this technical solution that filter elements can be manufactured in a simple manner and the resulting filter paper scrap is minimized. The filter elements with a polygonal configuration, wherein n>2, are finally inserted into a housing with an outer wall that is at least partly curved or has a polygonal configuration and a gap between the outer edges of the filter element and the housing wall is preferably filled with foam or filled by casting. The filter element separated from the pleated preform in this case has a polygonal configuration such that at least three corners are formed at the outer edges in a top view of the pleated preform, i.e., in a view of the tips or the recesses of the folds.

The filter element can be separated from the pleated preform both by means of cutting methods, and especially so-called laser cutting, by ultrasound or with mechanical cutters, as well as with suitable punching methods.

According to a special embodiment of the present invention, the pleated preform and/or the filter element already separated from the pleated preform are connected to at least one spacer for stabilizing the fold shape. For establishing the necessary stability, traces of glue are applied, for this purpose, to the pleated preform or the already separated filter element. Moreover, it is conceivable that additional network layers, which are also folded or subsequently applied, are provided, with which an inherent stability of the folds is ensured. According to another embodiment, provisions are made for a spacer to be configured in the form of a comb, which is used in the already arranged folds for the stabilization thereof.

According to another embodiment of the present invention, provisions are made for a glue to be provided as means for creating an edge seal in at least some sections and traces of glue, which act as spacer and/or as edge seal, to be applied to the pleated preform in at least some sections. In this case, the traces of glue are preferably first applied to the pleated preform and then the filter elements are separated from the pleated preform such that the interfaces are in the area of the traces of glue. In this way, it is ensured in a comparatively simple manner that the filter elements separated from the pleated preform immediately have an edge seal and no further method steps are necessary for creating a suitable edge seal.

The filter paper, which is folded and thus the desired pleated preforms are prepared, is preferably made available as roll material. The manufacture of filter elements according to the present invention, in which filter paper is folded and the filter elements are finally separated from the pleated preforms, which preferably already have spacers and/or suitable traces of glue, generally minimizes the filter paper waste or scrap. This is preferably achieved by the individual filter elements having a triangular, a square or especially a hexagonal outer contour. In this case, the individual cut surfaces preferably lie directly next to one another, the separation preferably being carried out in the area of traces of glue, so that, on the one hand, the waste is reduced to a minimum and the separated, polygonal filter elements already have an edge seal at their outer edges. As an alternative, according to the present invention, the edge seal can be created in a housing or in a mold by foaming.

With the method according to the present invention, the quantity of filter paper scrap material is thus minimized and at the same time a method for preparing an edge seal for polygonal pleated preforms, especially for hexagonal pleated preforms, is provided.

According to a special embodiment of the present invention, the preparation of the edge seal for the polygonal pleated preforms is ensured by a relative motion of glue nozzles to the filter paper and to the pleated preforms. This relative motion is preferably carried out synchronously with the folding of the paper, as a result of which a uniform and repeatable application of glue to the edges of the pleated preform and especially to the outer edges of the later separated filter elements is ensured. Provided that the filter elements shall have a hexagonal outer contour, the application of the glue is carried out in a zig-zag-shaped manner.

In order to achieve a sealing of the filter against the housing in an especially suitable manner, a gap between the filter element and a housing wall is filled with foam and/or filled by casting in a special variant of the present invention. In this case, the sealing is preferably carried out by means of foam, especially with a polyurethane foam. An edge seal is reliably produced in this way regardless of what gap shapes or gap dimensions, which may deviate due to production tolerances, are present. As an alternative or in addition, it is conceivable to inject an adhesive into the gap between the filter element and the housing inner wall. A hot glue is preferably used as adhesive in this case.

According to an alternative technical solution, the pleated preform is not inserted into a housing and connected to same in at least some sections, but rather the pleated preform is foamed in a suitable manner, so that an outer contour is produced and the pleated preform can be connected to a filter housing, a mask or another breathing port or to a blower filter device, preferably by clamping, in a particle-impermeable manner. In this connection, it is, in principle, insignificant what geometric shape the outer contour has. Above all, it is not necessary that a cross section of the outer contour have a polygonal edge. Rather, it is likewise conceivable in this case that the outer contour or the edge of the set foam is curved in at least some sections, the pleated preform being enclosed by a molded foam element in an exceptionally suitable manner, which element makes possible a particle-impermeable seal against a circular filter housing.

According to another special embodiment of the present invention, an area, which connects directly to the outer contours of the filter element, is freely filled with foam. No defined outer contour is thus provided. By using a suitable foam material, especially a polyurethane foam, it is ensured that the necessary edge seal of the filter element is achieved without special steps having to be taken. In this connection, it is absolutely conceivable that the area, in which a free filling with foam is carried out, is located within a gap between the filter element and a wall of the housing, which has such a width that it is not completely filled with foam or filled by casting, but rather the foam or adhesive, which ensures the edge seal, is only located within the gap.

In another variant of the present invention hexagonal pleated preforms may each be inserted based on a need in housings with different contours. By using an adhesive or foam for filling the gap between the pleated preform (or filter element) and the housing, different housing shapes and gap dimensions can be used in this case. Moreover, molded foams may be used for producing a defined outer contour of the foam in order to insert the filter element foamed in this way as a pre-arranged assembly unit into the housing of the particle filter or of a combination filter. At the same time, a reliable seal between the filter element and the housing is ensured by this foam, and especially by a light press fit between the foam and the countercontour of the housing.

According to another variant of the present invention, a direct connection to the breathing port is established by the molded foam also representing the connecting elements or also incorporating the corresponding inserted parts and at the same time sealing in a particle-impermeable manner. As has already been suggested the gap may be filled by free filling with foam without defined outer contour for establishing the particle-impermeable connection of the filtering element and housing. Likewise an intermediate element may be provided, which is in turn inserted, for example, into a combination filter and sealed there.

The present invention is explained in greater detail below without limiting the general idea of the invention on the basis of special embodiments with reference to the figures. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
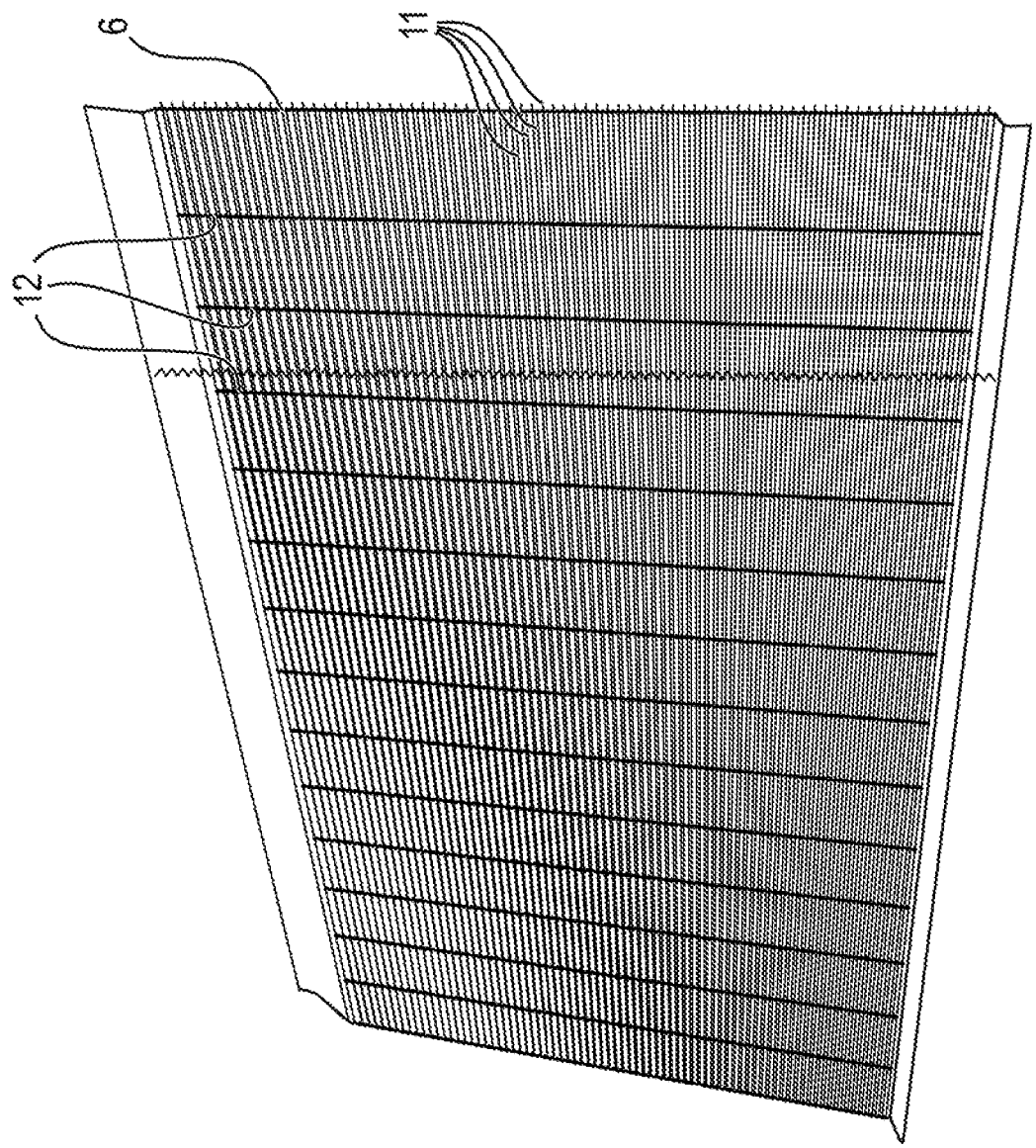
FIG. 1 is a perspective view showing a pleated preform with applied traces of glue.

Referring to the drawings, FIG. 1 shows in a perspective view a plate of parallel folds, which has been prepared from a filter paper which is at first made available as a roll material. In order to produce the needed filter elements 2, parallel folds 11 are first inserted into the roll material. The plate of parallel folds is split into individual pleated preforms 6 and finally the filter elements 2 each with the needed outer contour are separated from the pleated preform 6.

In order to ensure a sufficient edge seal after separating the needed filter elements 2 from the pleated preform 6, traces of glue 12 have been applied to the plate of parallel folds already before producing the individual pleated preforms 6, which ensure at the same time an inherent stability of the folds 11 produced. Optionally, the edge gluing 5 is carried out at a later time, especially by means of the foam 10 or adhesive 13 used for establishing a connection between the filter 1 and the housing 3.

Filter elements 2 are finally separated from the pleated preform 6 and sealed in a housing 3 by a connection being established between the outer edges 7 of the filter element 2 and the housing 3 of a filter 1 by means of foam 10 or hot glue 13. In this connection the filter element 2 may be inserted into a correspondingly provided housing component and foam may be applied or a foam 10 or an adhesive 13 may be embedded at the outer edges 7 of the filter element 2, especially in a gap 9 between the outer edges 7 of the filter element 2 and a component wall. In the alternative the outer edges 7 of the filter element 2 may be enclosed with a foam 10, preferably such that an element with a defined outer contour is formed, and to connect the filter element 2, that is embedded in the foam 10, to a housing component, especially by clamping in. In this case, it is, in principle, insignificant whether the filter element has an outer contour with a plurality of corners, the circumferential surface is at least partly curved, or else the flow cross-sectional surface of the filter element 2 has an actually circular configuration.

According to a first aspect of the present invention, a plurality of filter elements 2 are separated from a pleated preform 6, which have at least three, preferably six corners in a plane at right angles to the principal inflow direction of the filter 1. These filter elements 2, which are polygonal in relation to the contour of the outer edges 7, can now each be inserted into a housing 3.

The housings 3 being used often have a curved housing outer wall in at least some sections. In this case, it is deliberately accepted that a gap 9 remains between the housing wall 4 and the inserted filter element 2. Such a gap 9, between the filter element 2 and the housing wall, is entirely or partly filled with a foam 10 or adhesive and a reliable edge seal 5 is produced after the setting of the foam 10 or adhesive 13.

In this connection, the gap 9 may be filled entirely or else, for example, a foam or an adhesive bead may be embedded by means of free foaming such that the filter element 2 is fixed within the housing 3 and at the same time is sealed outwardly to the extent necessary.

Figure 2:
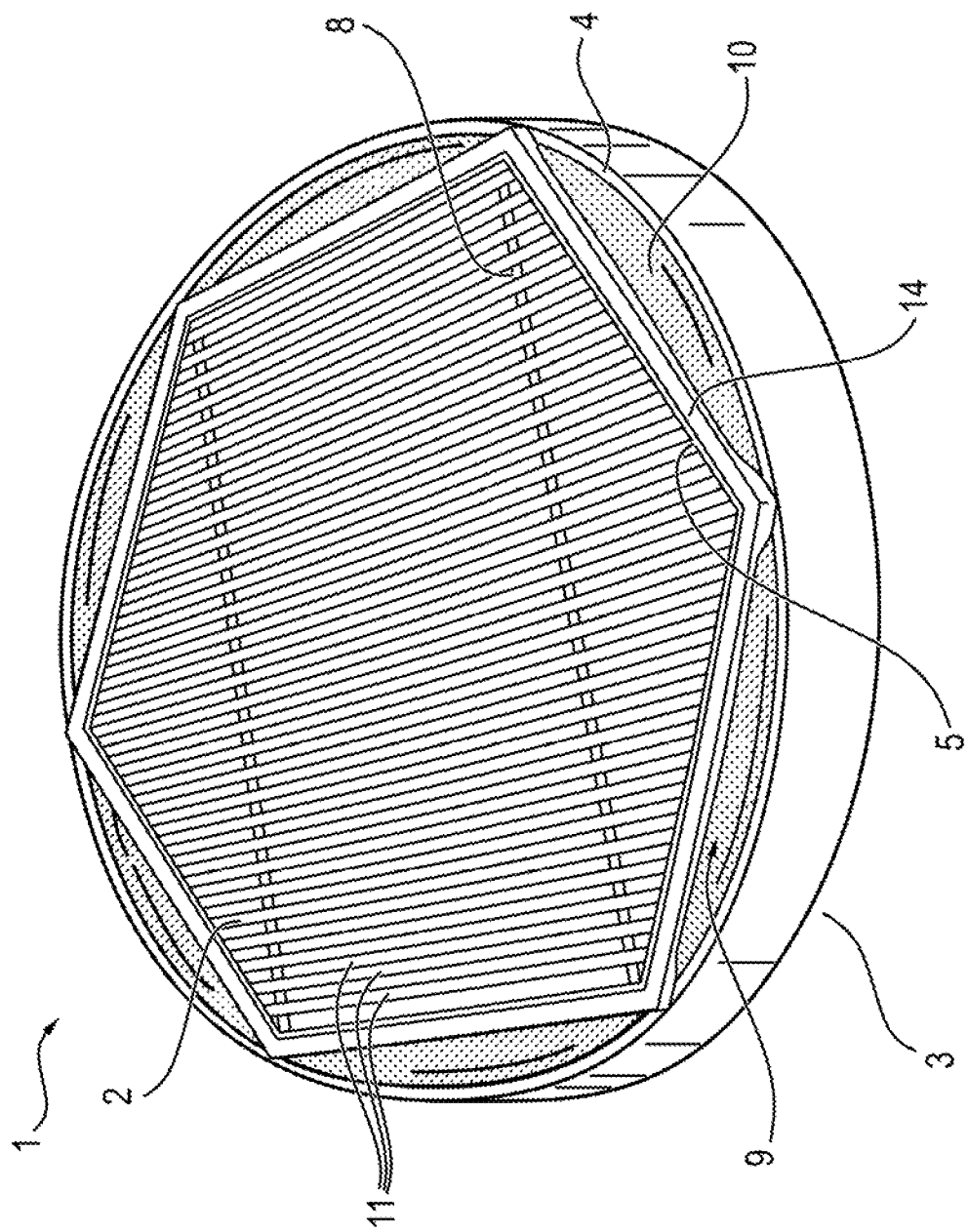
FIG. 2 is a perspective view showing a filter with hexagonal filter element with additional edge seal made of plastic, which is embedded into the filter housing.

In the exemplary embodiment shown in FIG. 2, a circular housing 3, into which a filter element 2 with a hexagonal outer contour is inserted, is provided. In this case, the hexagonal filter element 2 has a plastic frame 14, which encloses the filter element 2 at its outer edges 7 and thus likewise has a hexagonal contour. The filter element 2 is connected in a particle-impermeable manner to the plastic frame 14, so that, in principle, no further sealing is necessary. In the exemplary embodiment being shown, the filter element 2 is arranged with the plastic frame 14 within a filter housing 3 with a circular outer contour, the filter element 2 with the plastic frame 14 having been foamed with the formation of a molded foam element 15 and finally having been fixed together with the molded foam element 15 in the filter housing 3 by means of clamping in against the housing wall 4. It is, nonetheless, generally conceivable to additionally provide an edge seal, which was applied by means of glue, which was originally applied to the filter paper to be folded or the pleated preform 6, at the outer edges of the filter 2.

Figure 3:
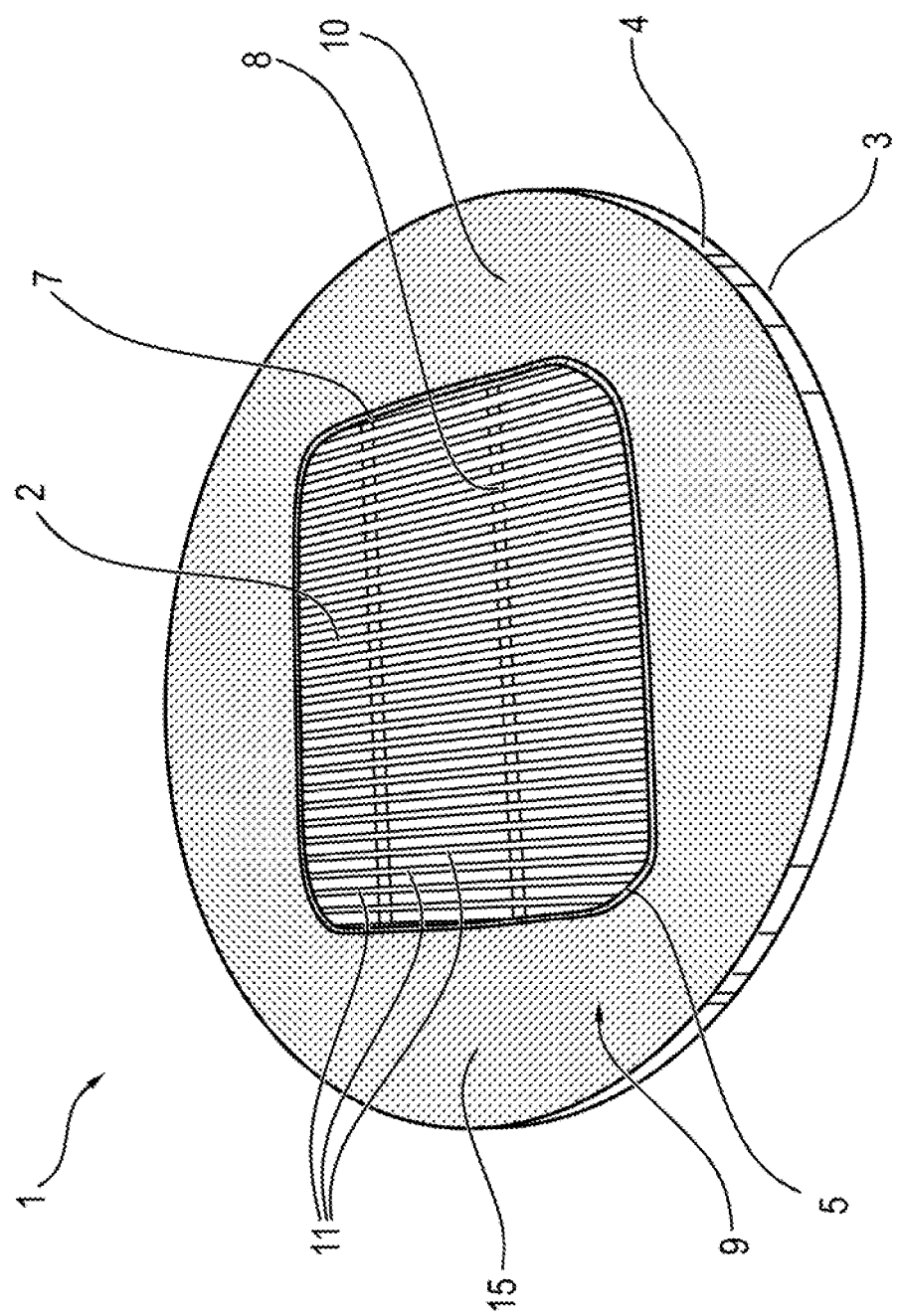
FIG. 3 is a perspective view showing a foamed filter element, which has obtained a defined outer contour due to the molded foam and has been inserted into a circular housing.

Moreover, FIG. 3 shows a filter housing 3 with a circular cross section, into which a filter element 2 is inserted. The filter element 2 was in this case foamed such that the filter element 2 has been fixed in the housing 3 by clamping in together with the molded foam element 15, which, on the one hand, ensures an edge seal and, on the other hand, ensures the sealing against the housing wall 4. The outer diameter of the molded foam element 15, compared to the inner diameter of the housing 3, preferably has a slight oversize for this purpose, so that the filter element 2 is securely clamped in the housing with the molded foam element 15.

Figure 4:
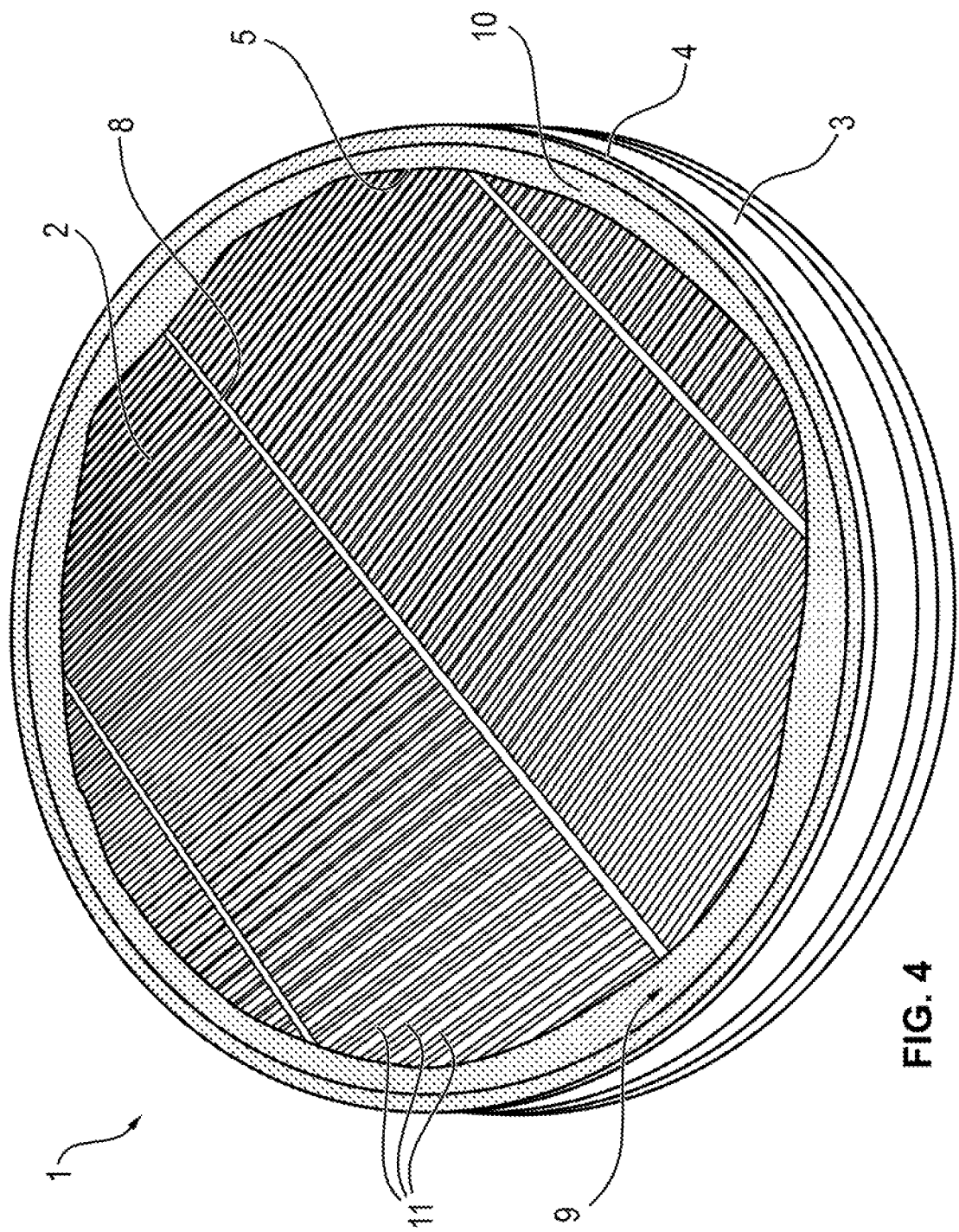
FIG. 4 is a perspective view showing an almost circular filter element embedded into a circular housing.

FIG. 4 shows a filter element with a circular outer contour which has been fixed in a filter housing 3 with a likewise circular outer contour. In this special technical configuration, a gap 9 between the outer edge 7 of the filter element 2 and the housing wall 4 has been filled by means of a foam 10. The foam fills the gap 9 entirely and hereby ensures both an edge seal 5 of the filter element 2 and the necessary fixing of the filter element 2 within the housing 3.

Figure 5:
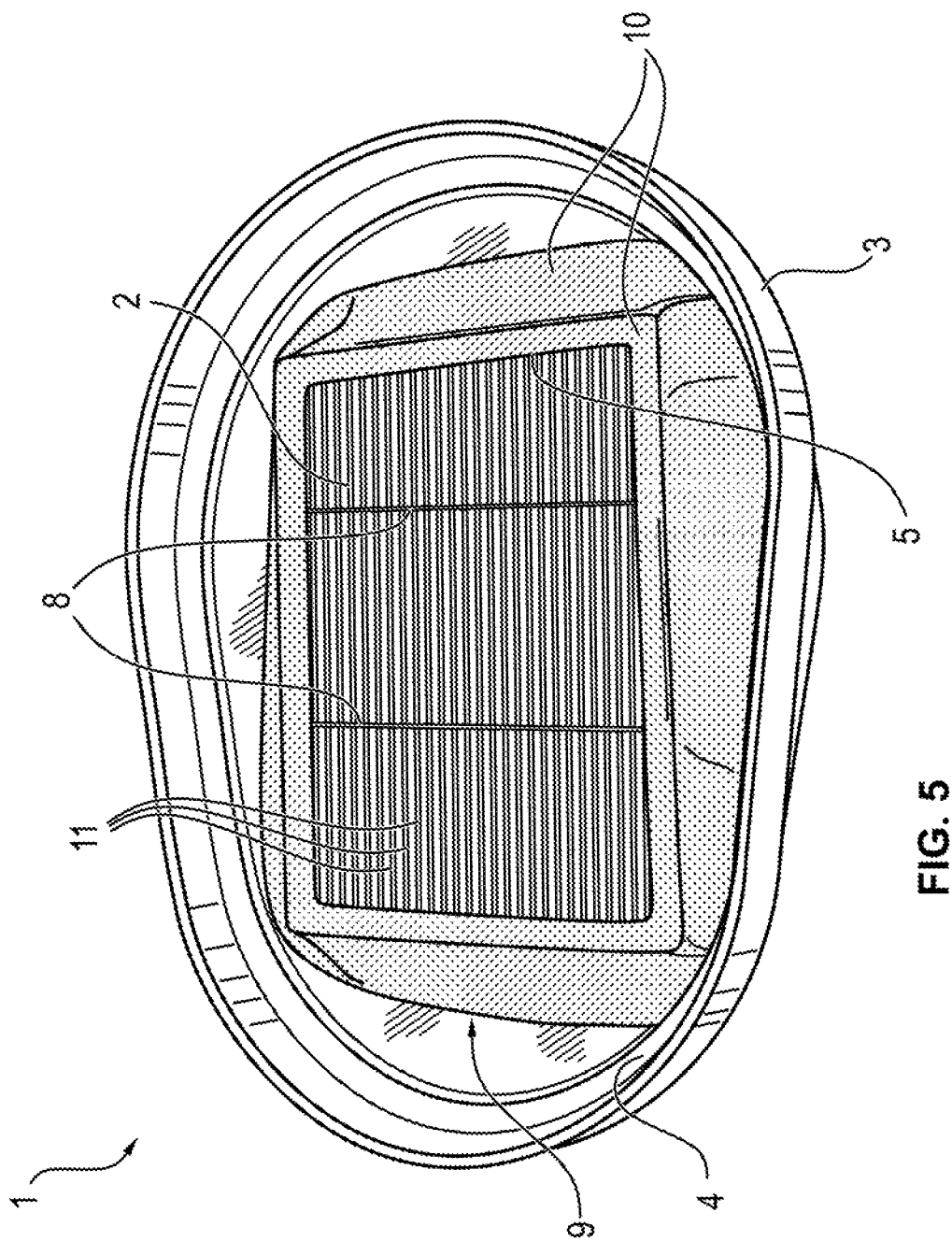
FIG. 5 is a perspective view showing a filter element, which is fixed by means of free foaming in the housing and is sealed against the housing.

FIG. 5 shows a filter housing 3 that does not have a circular cross section, but rather only an outer contour curve in at least some sections, as it is frequently used especially in filters for so-called half masks. For manufacturing the respirator filter 1, a filter element 2 with a polygonal outer contour is first manufactured and this element is inserted into the housing 3. For fixing the filter element 2, the filter element 2 is freely foamed and the gap 9 between the filter element 2 and the housing wall 4 is not filled entirely, but rather the necessary quantity of a suitable material, which also ensures the necessary edge seal 5, is embedded by means of free foaming. In this way, a type of foam bead is produced, which completely encloses the filter element 2 and fixes same within the housing. As an alternative or in addition, a sealing of the edges can be produced in this case by providing glue at the outer edges 7.

As the above embodiments have shown, the solution according to the present invention is, above all, characterized in that a fixing of the filter element 2 in the filter housing 3 with simultaneous sealing of the edge 5 of the filter element. This can be carried out in a relatively simple manner by using foam 10 or liquid adhesive 13. A great advantage in this case as well is that the filter housing 3 and the filter elements 2, which have different outer contours, can be combined with one another in a simple, cost-effective and yet process-safe manner.

According to a special embodiment of the present invention, a polygonal filter element 2 is inserted into a filter housing 3, which has a curved outer wall in at least some sections. In this case, it can be deliberately accepted that a gap 9 remains between the housing wall 4 and the filter element 2, since both the fixing of the filter element 2 within the housing 3 and the sealing of the edge by embedding a foam 10 or an adhesive 13, which can be injected, is ensured. As mentioned, the gap does not have to be filled entirely in any case.

Compared to prior-art respirator filters, the technical solution according to the present invention is characterized in that considerable process improvements can be achieved by using foams or liquid adhesives in the area of the filter element outer edges during the production of filters. Further, the filter material waste or scrap is reduced to a minimum by using polygonal filter elements.

While specific embodiments of the invention have been shown and described in detail to illustrate the application of the principles of the invention, it will be understood that the invention may be embodied otherwise without departing from such principles.

APPENDIX

List of Reference Numbers

1 Filter
2 Filter element

3 Filter housing
4 Housing wall
5 Edge seal
6 Pleated preform
7 Outer edge of the filter element
8 Spacer
9 Gap
10 Foam
11 Folds
12 Traces of glue
13 Adhesive
14 Plastic frame
15 Molded foam element

What is claimed is:

1. A filter with a filter element manufactured by the steps comprising:
    providing a flat paper material;
    folding the flat paper material to form a pleated preform;
    separating the pleated preform into at least one filter element;
    providing a housing;
    inserting the filter element into the housing;
    establishing a connection between the inserted filter element and the housing at least at some points, by applying a foam or an adhesive or both a foam and an adhesive to an outer edge of the filter element, which outer edge is arranged on a circumference of the filter element, for the at least partial sealing of the edge, which sealing establishes the connection of the filter element to the housing in at least some sections, said applying of the foam includes foaming the outer edge of the filter element to create a seal to entirely seal the outer edge of the filter element to the housing;
    providing the filter as a part of a gas mask, in a breathing air supply unit, in a blower filter device, or in a medical device; and
    disposing the filter element in the filter of the gas mask;
    wherein the steps of establishing the connection of the filter element to the housing with the circumferential sealing of the edge are carried out in one working step.

2. A filter with a filter element in accordance with claim 1, wherein:
    the step of separating the pleated preform into at least one filter element comprises providing the filter element with at least three corners in a plane, which plane is at right angles to a principle inflow direction of the filter;
    the housing is provided with a peripheral wall with a plurality of curved sections or at least three corners; and
    the filter element is inserted into the housing with the housing wall enclosing the filter element at filter element outer edges.

3. A filter with a filter element in accordance with claim 1, wherein the filter element has at least one connection to connect the filter element to a gas mask, to a breathing air supply unit, to a blower filter device or to a medical device by an at least partial rotating motion.

4. A filter with a filter element in accordance with claim 1, wherein:
    the seal at the outer edge of the filter element is produced after setting of the foam.

5. A filter with a filter element, the filter comprising:
    a housing having a curved wall configured to insert into a mask;
    a pleated filter element arranged in said housing, said filter element having an outer edge arranged on a circumference of said filter element, said outer edge being polygonal and spaced from said housing by a gap;
    one of a foam and an adhesive arranged in said gap, said one of said foam and said adhesive being connected to said outer edge of the filter element, said one of said foam or said adhesive being connected to said housing, said one of said foam or said adhesive being configured to both connect said outer edge of said filter element to said housing, and entirely seal said outer edge to said housing.

6. A filter with a filter element in accordance with claim 5, wherein:
    said inserting of the filter element produces a gap between the outer edge and the housing;
    said applying of the foam includes having the gap entirely foamed to both seal the outer edge to the housing and fix the filter element in the housing.

7. A filter with a filter element in accordance with claim 5, wherein:
    said foam is configured to both connect and entirely seal said outer edge to said housing.

8. A filter with a filter element in accordance with claim 5, wherein:
    said adhesive is configured to both connect and entirely seal said outer edge to said housing.

* * * * *